US012763184B2

(12) United States Patent
Lauwers et al.

(10) Patent No.: US 12,763,184 B2
(45) Date of Patent: Oct. 13, 2026

(54) CLINICAL SUPPLY PACKS WITH ELECTRONIC LABELING

(71) Applicant: JANSSEN PHARMACEUTICA NV, Beerse (BE)

(72) Inventors: Roger Lauwers, Beerse (BE); Karl Jacobs, Beerse (BE)

(73) Assignee: Janssen Pharmaceutica NV, Beerse (BE)

( * ) Notice: Subject to any disclaimer, the term of this patent is extended or adjusted under 35 U.S.C. 154(b) by 43 days.

(21) Appl. No.: 18/021,328

(22) PCT Filed: Aug. 27, 2021

(86) PCT No.: PCT/EP2021/073739

§ 371 (c)(1),
(2) Date: Feb. 14, 2023

(87) PCT Pub. No.: WO2022/043494

PCT Pub. Date: Mar. 3, 2022

(65) Prior Publication Data

US 2023/0307110 A1 Sep. 28, 2023

Related U.S. Application Data

(60) Provisional application No. 63/071,794, filed on Aug. 28, 2020.

(51) Int. Cl.

*G16H 20/13* (2018.01)
*G16H 10/20* (2018.01)
(Continued)

(52) U.S. Cl.

CPC ............. *G16H 20/13* (2018.01); *G16H 10/20* (2018.01); *G16H 40/67* (2018.01); *G16H 70/40* (2018.01)

(58) Field of Classification Search

CPC ........ G16H 20/13; G16H 40/67; G16H 70/40; G16H 10/20

See application file for complete search history.

(56) References Cited

U.S. PATENT DOCUMENTS

| | | | |
|---|---|---|---|
| 4,476,381 A | 10/1984 | Rubin | |
| 7,752,085 B2 | 7/2010 | Monroe | |

(Continued)

FOREIGN PATENT DOCUMENTS

| | | | |
|---|---|---|---|
| AU | 2014271345 A1 * | 1/2015 | ............. A61B 5/021 |
| CN | 205162205 U | 4/2016 | |

(Continued)

OTHER PUBLICATIONS

• Huai-Kuei Wu et al., A smart pill box with remind and consumption confirmation functions, 2015 IEEE 4th Global Conference on Consumer Electronics (GCCE) 658-659 (Feb. 4, 2016) (Year: 2016).*

(Continued)

*Primary Examiner* — Jordan L Jackson
(74) *Attorney, Agent, or Firm* — Craig M. Brown

(57) ABSTRACT

Clinical supply packs may be provided with electronic paper labels displaying information updated based on internal sensors and inputs of the clinical supply pack or communications with an external communication device, where the communication device is in communication with a central system. Display information may include multilingual data provided to supply packs after they are sealed for distribution, and may include updated dosing regimens and clinical trial updates provided after dispensing.

19 Claims, 10 Drawing Sheets

(51) Int. Cl.

| | |
|---|---|
| ***G16H 40/67*** | (2018.01) |
| ***G16H 70/40*** | (2018.01) |

(56) References Cited

U.S. PATENT DOCUMENTS

| | | | | |
|---|---|---|---|---|
| 8,165,892 | B2 * | 4/2012 | Carter | G16H 70/40 705/2 |
| 8,391,104 | B2 * | 3/2013 | de la Huerga | A61J 1/1437 235/375 |
| 9,492,355 | B2 | 11/2016 | Ratnakar | |
| 9,775,780 | B2 | 10/2017 | Afsarifard et al. | |
| 9,814,653 | B2 | 11/2017 | Lehmann et al. | |
| 10,026,296 | B2 | 7/2018 | Fateh et al. | |
| 10,252,002 | B2 * | 4/2019 | Haider | A61M 5/14244 |
| 10,278,287 | B2 | 4/2019 | Wilson et al. | |
| 10,751,259 | B1 * | 8/2020 | Dutta | A61J 7/0472 |
| 2002/0038392 | A1 | 3/2002 | De La Huerga | |
| 2002/0089434 | A1 | 7/2002 | Ghazarian | |
| 2007/0056871 | A1 | 3/2007 | Griffiths et al. | |
| 2010/0164710 | A1 | 7/2010 | Chung et al. | |
| 2011/0279271 | A1 | 11/2011 | Monroe | |
| 2014/0021253 | A1 | 1/2014 | Carson et al. | |
| 2015/0145672 | A1 * | 5/2015 | Chu | G08B 21/24 340/539.11 |
| 2017/0248401 | A1 | 8/2017 | Isom et al. | |
| 2018/0125761 | A1 | 5/2018 | Conlon et al. | |
| 2019/0042702 | A1 * | 2/2019 | Chandramouli | A61B 5/0205 |
| 2020/0219594 | A1 | 7/2020 | Angiuoli et al. | |
| 2020/0335195 | A1 * | 10/2020 | Fryman | A61M 5/484 |

FOREIGN PATENT DOCUMENTS

| | | | |
|---|---|---|---|
| JP | 2017041224 | A | 2/2017 |
| WO | WO 2009/056945 | A2 | 5/2009 |
| WO | WO 2014/187484 | A1 | 11/2014 |

OTHER PUBLICATIONS

International Preliminary Report and Written Opinion, dated Feb. 28, 2023, International Application No. PCT/EP2021/073739, pp. 1-11.

International Search Report dated Dec. 8, 2021; International Application No. PCT/EP2021/073739.

* cited by examiner

CLINICAL SUPPLY PACKS WITH ELECTRONIC LABELING

CROSS REFERENCE TO RELATED APPLICATIONS

This application is the U.S. national stage of PCT Application No. PCT/EP2021/073739, filed Aug. 27, 2021, which claims priority to U.S. Provisional Patent Application No. 63/071,794, filed Aug. 28, 2020, the entire contents of each of which are hereby incorporated by reference as if set forth in their entirety herein.

BACKGROUND

Pharmaceutical supply packages, also known as medication kits or clinical supply packs, that carry pharmaceutical product. For instance, the pharmaceutical product is often provided as pills that are stored in discrete sealed storage containers, also known as blisters, of the wallet. In order to access the pharmaceutical product, the patient typically opens the package and slides out the wallet, thereby exposing the blisters. Individual pharmaceutical product is removed from the respective blisters for consumption as directed.

Packages used for clinical trials can contain active pharmaceutical product or a placebo. Further, the dose or concentration of the active pharmaceutical product can vary between packages delivered to different patients according to the requirements for the clinical trial. Moreover, the dose or concentration of the active pharmaceutical product supplied to an individual patient can vary from package to package and even from pill to pill inside the same package.

Conventionally, data associated with the package that is relied upon by the patient can be printed on labels of the packaging itself, or can be printed onto separate sheets that can be provided as inserts in the package, or can be otherwise carried by the package. The data can include the expiration dates of the pharmaceutical product, safety information, storage information, instructions for consumption of the pharmaceutical product, and the like. It is recognized that the data is printed in accordance with the applicable regulations of the country to which the package is to be shipped. Thus, the data is printed in the language or languages required by the regulations of the particular country.

Information printed on a label may include other information, such as a patient name, clinician name, serialization number, prescribed dosage, and the like. In the case of clinical trials, such information may be handwritten.

SUMMARY

Clinical supply packs may be provided with electronic labels, including electronic paper labels, which may be used, in junction with an external communication device, to perform supply pack labeling after packaging for distribution, whereby patient, safety, and/or clinical trial information is added to label after a pack is assembled, and after packs are collected into a multipack for shipment, for example.

Electronic labeling may be further used for custom language displays, which are tailored for patients and care givers, in addition to regulatorily required labeling. For example, information may be provided to a supply pack for display in three languages, where information in a first language is displayed to meet regulatory requirements in a country or region where a patient receive treatment. Information may also be displayed in a second language or third language, as selected by a user of the supply pack.

Electronic labeling may be used for the dynamic presentation of static information, e.g., for browsing through multipage information, and may be used to display dynamic information, such as expiry, storage conditions, or usage of clinical materials.

Electronic labeling may be used to alter information during usage of a supply pack by a client, e.g., whereby a dosing regimen or other protocol information is provided or altered by an attending physician or clinical investigator, for example, and the new information is displayed on the supply pack itself.

Electronic labeling may be used to redirect or reuse clinical materials, e.g., by providing new patient, safety, and/or clinical trial information at any time, including after manufacture, after distribution, and distribution, and after dispensing to the patient.

Continued use, redirection, and reuse of clinical materials may be contingent on use and storage information gathered by the supply pack or other equipment and systems.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to limitations that solve any or all disadvantages noted in any part of this disclosure.

BRIEF DESCRIPTION OF THE DRAWINGS

A more detailed understanding may be had from the following description, given by way of example in conjunction with the accompanying drawings.

DETAILED DESCRIPTION

Figure 1:
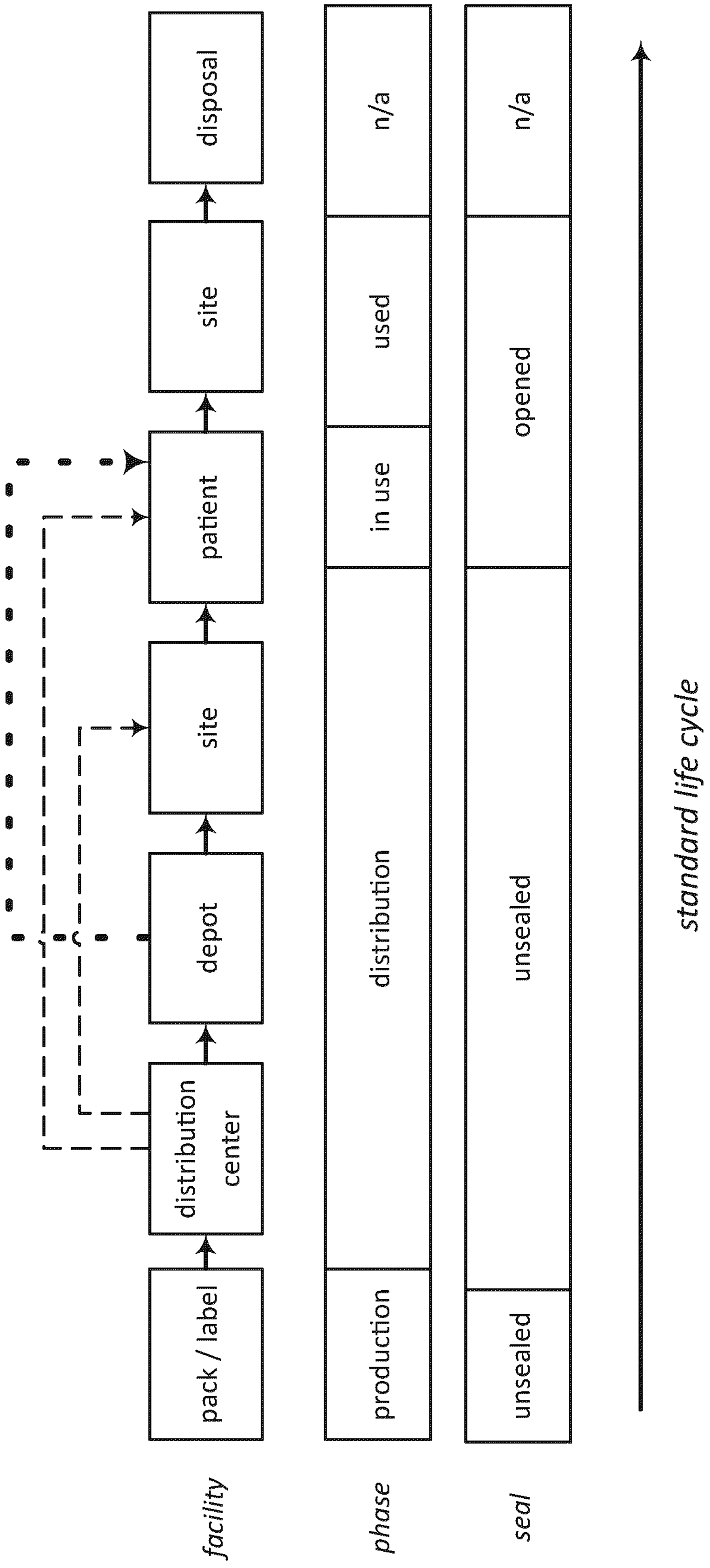
FIG. 1 is a block diagram of an example pharmaceutical supply life cycle.

Intelligent packaging for clinical supplies, including clinical trial materials, and the management thereof, are disclosed. FIG. 1 is a block diagram of an example pharmaceutical supply life cycle. Pharmaceutical materials, packaging, and labels are combined into clinical supply packs in a pack and label facility. Packs are typically sealed, e.g., with a quality seal, a shrink wrap, or the like, at the end of production. Traditionally, a supply pack may include printed materials including, for example, detailed storage, use, safety and other materials. In the distribution phase, sealed supply packs may move from a distribution center to a depot, then to a dispensing site, and ultimately to a patient. Alternatively, supply packs may be sent directly to a site or a patient directly from the distribution center, or from a depot to a patient for example.

In the distribution phase, before being dispensed for use by a patient, a supply pack will remain sealed. It will be unsealed for use by the patient. A used supply pack may be collected by a site, e.g., for analysis, or for transfer for safe disposal of the used materials.

Figure 2:
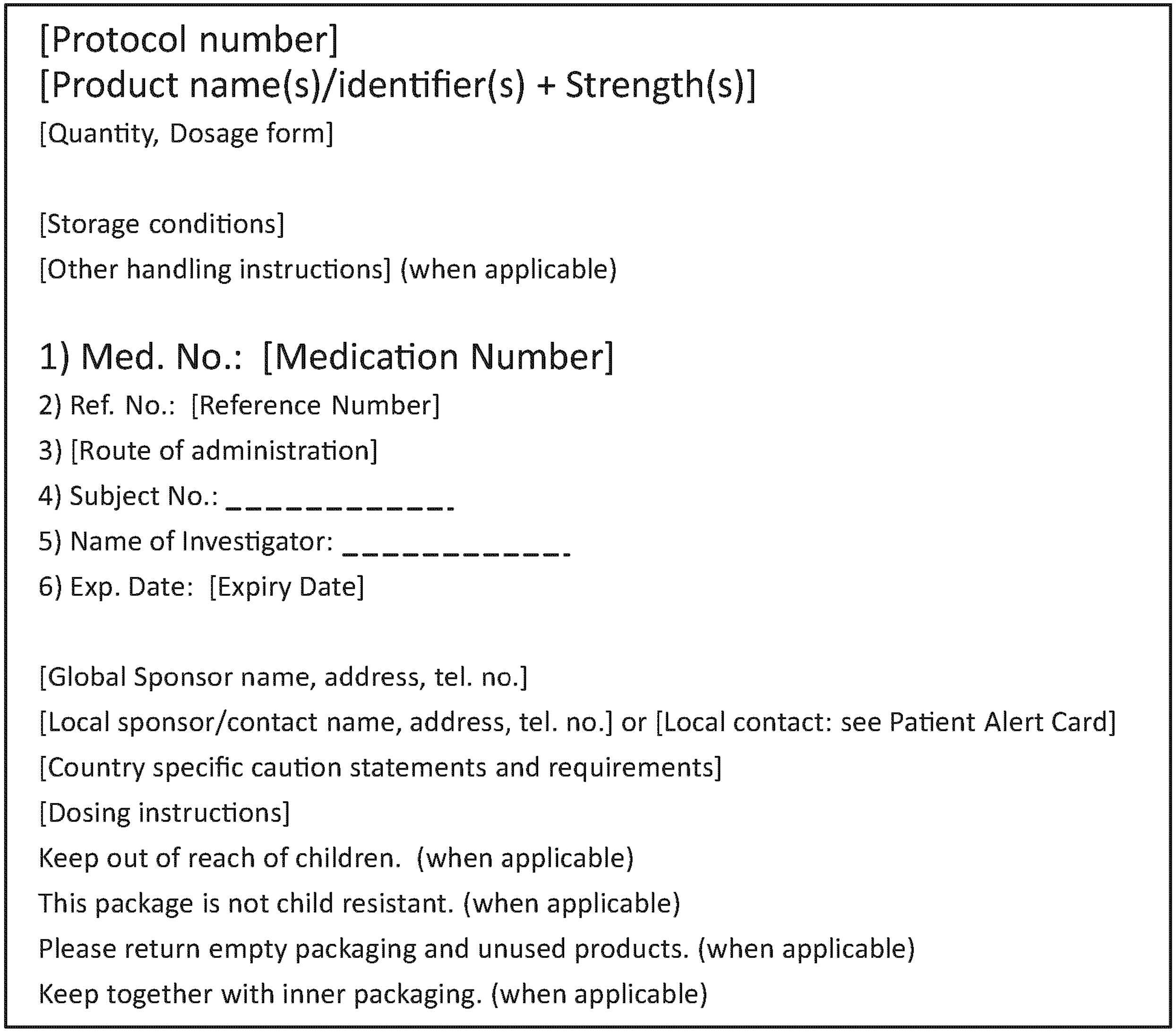
FIG. 2 is an example of information on a label of a pharmaceutical supply.

FIG. 2 is an example of information on a label of a pharmaceutical supply. In FIG. 2, the label is for a supply pack for a clinical trial. In this example, the label identifies the pharmaceutical product contained in the pack, e.g., by its product name or other identifier, quantity of product in the pack, and dosage form. Safety information, including storage and handling instructions is listed, as well as directions to keep out of the reach of children, whether the pack is child/tamper resistant, and instructions for disposition of unused product. For a clinical trial, a label may include protocol number or other identifier, medication number, reference number, route of administration, information regarding the global sponsor of the trial and the local sponsor of the trial. For prescription medicines that are not involved in a clinical trial, a label may alternatively include things like the name of the prescribing physician, dispensary, or the like, as well as the name of patient. In the example of FIG. 2, the patient is identified by a subject number, and the physician is the investigator or the trial. The label further includes an expiration date and dosing instructions.

In the example of FIG. 2, in manner of traditional clinical trial labels, the subject number and name of investigator are left blank to be filled by hand at the time of dispensing.

Figure 3:
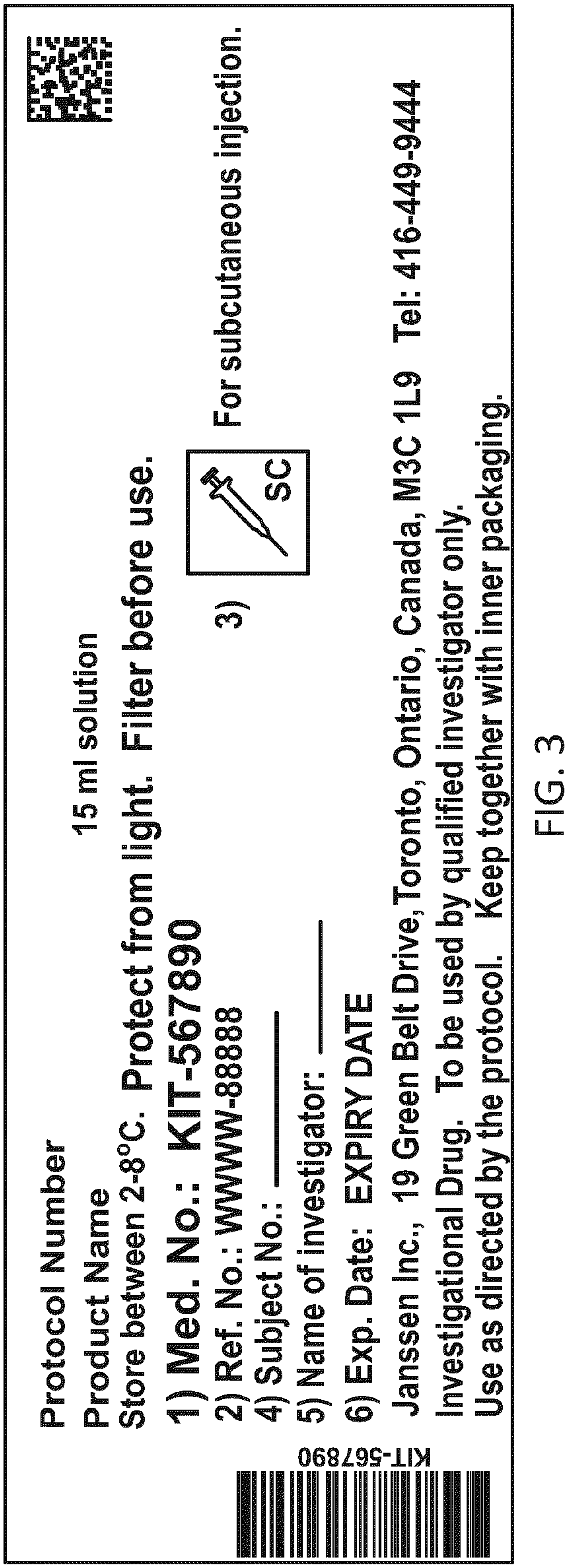
FIG. 3 is an example of a Canadian label in English.
Figure 4:
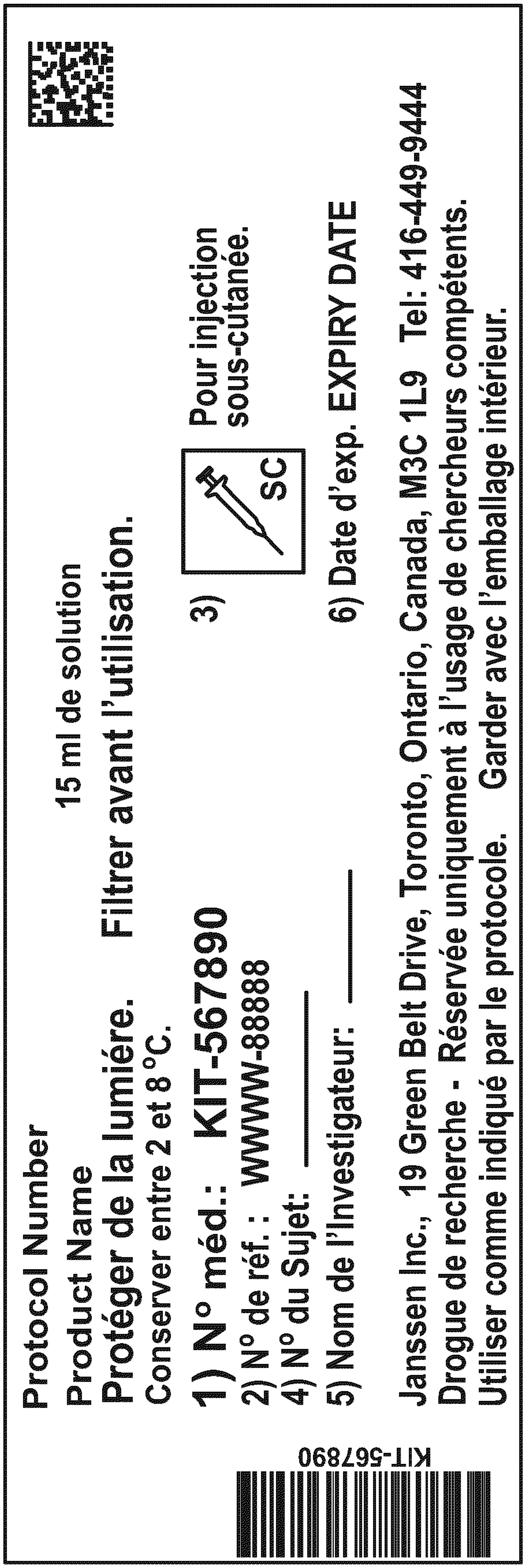
FIG. 4 is an example of a Canadian label in French.
Figure 5:
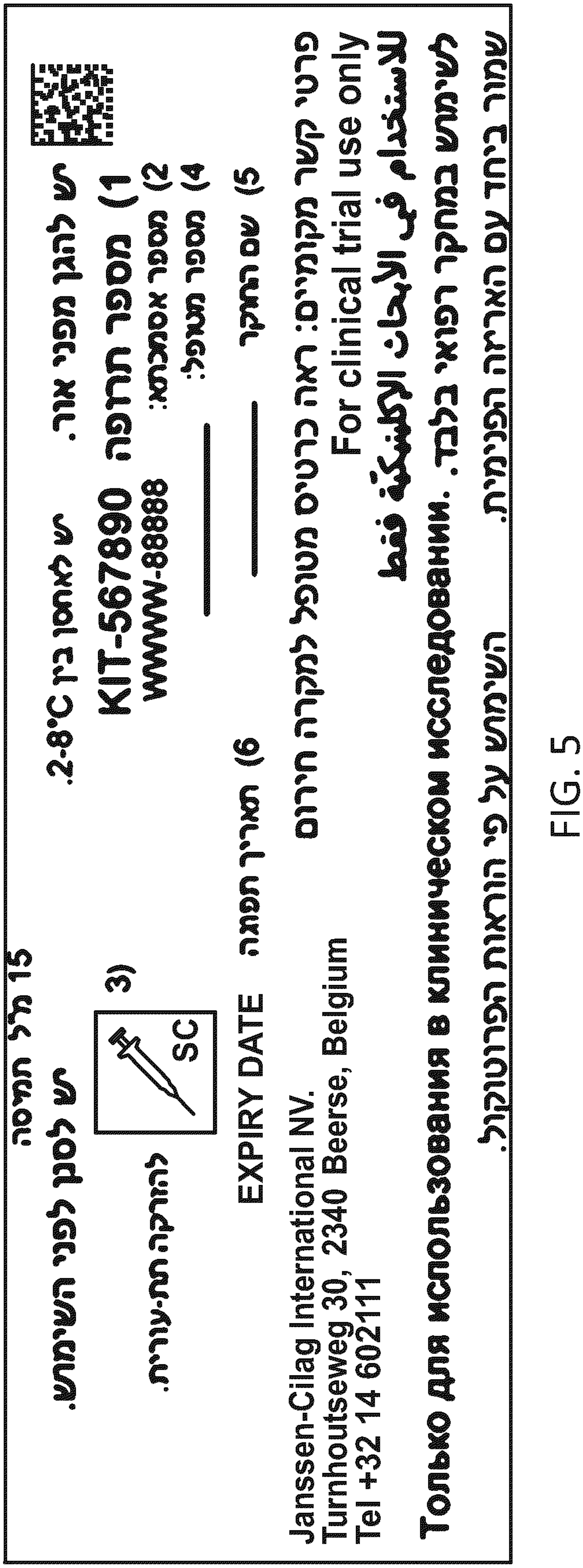
FIG. 5 is an example of an Israeli label in Hebrew, Russian, and Arabic.

The management of this data presents a number of challenges in coordinating pharmaceutical production, distribution, and dispensing. For example, in practice all the information on such a label may need to be translated into other language. This includes variable information, e.g., the expression of the month code in the expiry date. Some content is country specific, or specific to local sponsors. Some countries may require more content than others. For example, Germany requires a eudrag number in Germany. Some countries require specific statements in multiple languages on the same label. For example, Israel requires, on the same label, information to be presented in English, Hebrew, Arabic, and Russian. FIG. 3 is an example of a Canadian label in English. FIG. 4 is an example of a Canadian label in French. FIG. 5 is an example of an Israeli label in Hebrew, Russian, and Arabic. Serial numbers, such as the two-dimensional bar codes shown in the examples of FIGS. 3, 4, and 5 may be determined during production. Traditionally, in the case of clinical trials, protocol identification is determined when a clinical supply pack is assigned to a protocol. In case of pooling this can happen anywhere in the process, between production of the Clinical Supply Pack (earliest) and dispensing of the Clinical Supply Pack to a patient (latest).

Information provided with clinical supply packs, including label information, may be subject to change at any time. Practices for changing labeling information vary, e.g., from country to country, and practices are evolving.

Electronic labeling allows many options for both better initial labeling and for updating label information at any point in the supply pack life cycle. Further clinical supply packs may be configured to adjust their own labels independently, in response to conditions such as use, environment, and the passage of time, with or without the assistance of external devices.

For instance, serial numbers or other identifiers, may be displayed, e.g., as bar codes or in other formats, on electronic labels. Bar code serial numbers are commonly used to facilitate production, distribution, and dispensing clinical supply packs. However, with electronic labeling, the serial identifier of a clinical supply pack does not have to be static.

Traditionally, in a clinical trial, the investigator identification is determined when dispensing of the clinical supply pack to a patient. With electronic labeling, the association of a clinical supply pack to a patient, trial, or investigator, can be identified at any point in the life cycle, and the label adjusted accordingly. Re-assignment to a different protocol is possible.

Traditionally, patient identification is determined when dispensing a clinical supply pack to a patient. Clinical Supply Packs are commonly NOT produced for a specific patient, so prior to dispense there is no patient related label information available. However, with electronic labeling, patient specific clinical supply packs could be produced at a pack and label facility—or a distribution center or depot. Normally, once a clinical supply pack is labeled for use by a first patient, it is not relabeled for use by a second patient. However, with electronic labeling this is possible, and may be valuable to recover, for example, rare or valuable clinical supplies which are in good condition for transfer to the second patient.

Dosing instructions may have been determined already during production. However, it is also possible that dosing is only determined at the time of dispense to the patient. For example, based on the specific patient criteria, one of many possible regimens may be selected by physician/investigator, such as more or fewer pills per dosing, depending on patient age or weight.

Similarly, electronic labeling allows for the changing of the language or languages of the displayed information depending on where the clinical supply physically is currently, where it is destined to be sent, and where it will travel along the way. Even after being dispense, a patient or care giver may prefer to have information made available in a different language on the clinical supply pack electronic label. The language, format, and content of the information displayed on electronic label may be changed at any time, allowing determinations of the place and person using the clinical supply pack to be indicated or changed at any point in the product life cycle.

Figure 6:
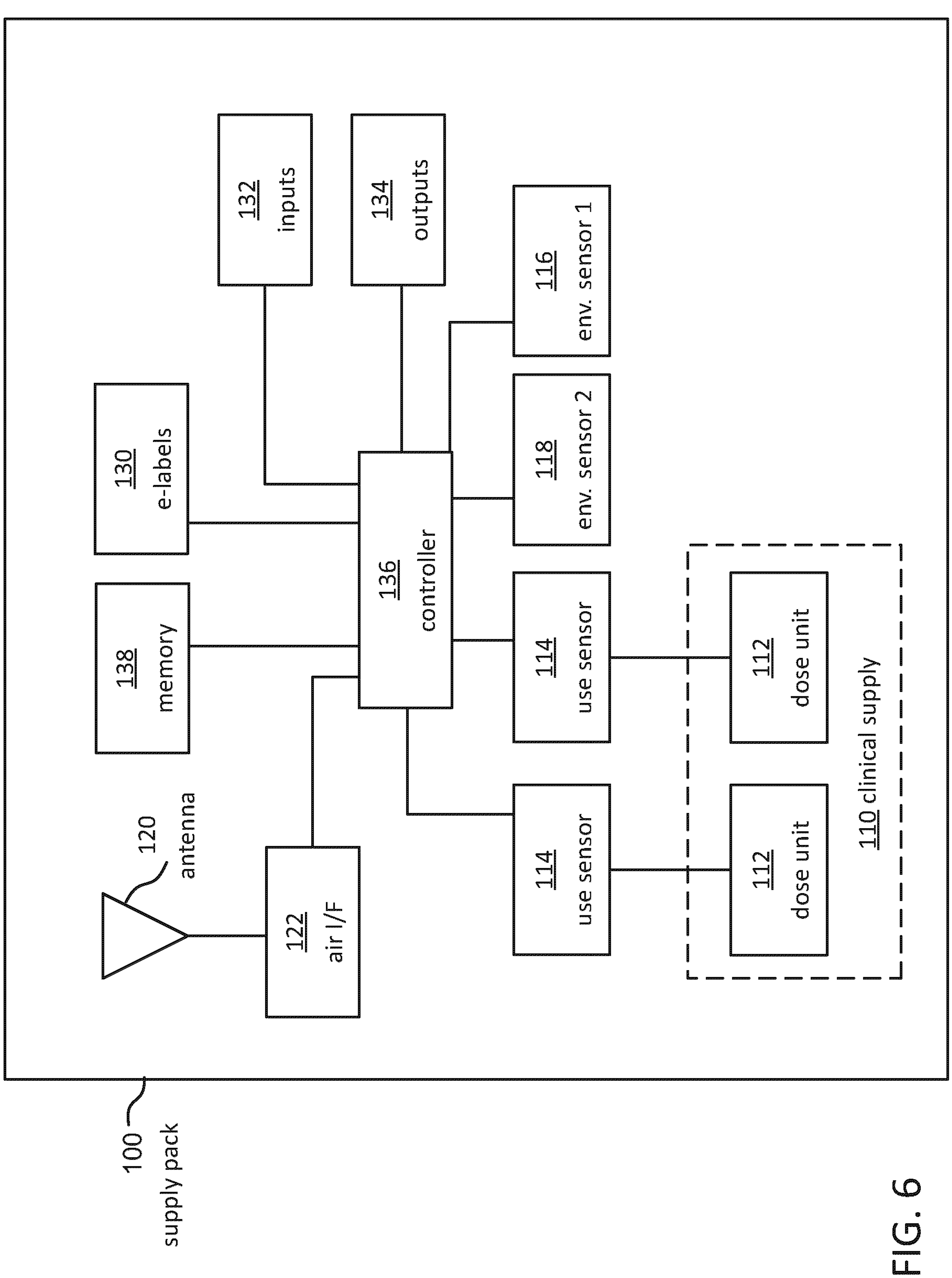
FIG. 6 is a block diagram of an example clinical supply pack.

Referring to FIG. 6, a clinical supply pack 100 includes a clinical supply 110 of pharmaceutical dose units 112. The clinical supply pack 100 can be configured as a smart supply pack having use sensors 114 that can be configured to detect the removal of the dose units 112 from the clinical supply pack. For example, the clinical supply 110 may take the form of a blister pack, e.g., a plastic tray with an array of indentations with a foil backing sealing doses of medication, such a pills or capsule, in each indentation. In this case, the use sensor 114 may simply be a wire which is broken by the breaking of the foil in the proximity of the indentation to allow for the removal of the dose unit 112. The supply pack 100 can include a controller 136, which can be a digital computing processor, that is used to control operations of various components of the supply pack. For instance, the controller 136 can be configured to determine either or both of the number of dose units 112 and the position of dose units 112 that have been removed from the clinical supply 110.

The use sensors 112 can be used by the controller 136 to collected use information including which dose is used and when it is used.

Alternatively, the clinical supply 110 may be an array of dose units 112 in the form of vials, syringes, or applicators containing liquid, powder, or gel material, for example, where the use sensors 114 detect removal or a level of material remaining in the vials, etc., or both, for instance.

Further, the clinical supply 110 may include a set of clinical supplies. For example, the clinical supply 110 may include a combination of items such as medical dose units, swabs, test strips, sample containers, needles, and the like, that are used for execution of a medical protocol over a period of time, such as adherence to a protocol during a course of treatment or medical trial.

In practice, the supply pack 100 may include a processor or a plurality of processors or controllers. Alternatively, or additionally, the supply pack 100 can include at least one processor that is integrated into various components of the supply back 100 in addition to, or instead of, a main controller. Similarly, in the example of FIG. 6, the supply pack 100 includes a memory, which may be used to store information and executable code used by the controller 136.

In practice, a supply pack 100 may have digital memory incorporated in various components of the supply pack 100 in addition to, or instead of, a main memory 138. It will be appreciated that processor and memory functions may be implemented in any number of ways by various technologies, including ROM and RAM memories, and/or structures such as dedicated execution hardware such as gate arrays, including field-programmable gate arrays, or the like.

In the example of FIG. 6, the supply pack 100 can further include an antenna 120 by which it may receive signals via the air interface 122. The air interface 122 may include an energy harvester which extracts energy incident on the supply pack 100 for use in the electronic operation of the supply pack 100. For example, the antenna 120 can be a radio antenna that operates in a near-field communication (NFC) band, and from which it extracts both energy and power. It is appreciated, however, that the supply pack 100 can alternatively employ any type of wired or wireless communications techniques, such as BlueTooth, an infrared link or other optical link, or wired serial communications, for example. For ease of use in distribution channels and patient treatment areas, non-line-of-sight communications may be preferred.

A clinical supply pack 100 may have multiple air interfaces. For example, it may have first interface communications with a communications device via WiFi, and a second interface by which it communicates with other clinical supply packs via near-field communication, or vice-versa. Further, clinical supply packs may operate in mesh, self-organizing, or master-slave networks, or the like.

Not shown in FIG. 6, the supply pack 100 may have other power sources, e.g., one or more batteries, a solar power panel, and/or a magnetic coupler to a base on which the supply pack is to be stored.

The controller 136 may be in communication with the various other components of the supply pack 100, which can include use sensors 114, environmental sensors 116 and 118, an air interface 122, memory 138, e-labels 130, inputs 132, and outputs 134. The controller 136 can perform operations to store, retrieve, and send information to and from the various other components and external devices via the air interface 122.

The controller 136, air interface 122, and/or executable code stored in the memory 138, may cause the supply 100 to implement security protocols to prevent unauthorized access to the supply back 100 via the air interface 122. For example, the supply pack 100 may be configured to allow access to, or modification of, stored information in accordance with security levels of users and/or authentication of users such as the patient.

In the example of FIG. 6, the supply pack 100 includes environmental sensors 116 and 118, which may be included to monitor the environment of the clinical supply 110 during distribution and/or in use. Environmental sensors may be located in proximity to the clinical supply 110 or elsewhere in the supply pack 100, and used to detect conditions relevant to the storage or administration of the dose units 112. Any number of environmental sensors may be employed. For example, environmental sensor 116 may be a temperature sensor, and may include a logging function to storage a record of temperatures at various times and/or a number of excursions beyond safe storage or use temperature. Environmental sensor 118 may be a vibration sensor useful in monitoring motion of the supply pack 100, e.g., to detect excursions from safe handling which may lead to the separation of dose unit 112 materials, such as colloids or suspensions. Further, environmental sensors may be used to detect, e.g., exposure to visible or UV light, or other radiation, or humidity, which may lead to the degradation of dose unit 112 materials in the clinical supply 110. Data from the environmental sensors 116 and 118 may be assessed by the controller 136, for example, to determine the fitness of dose units 112 the clinical supply 110 for use, e.g., whether dose units are to be deemed expired, unsafe, or suitable for current use. Data from the environmental sensors 116 and 118 may be stored by the controller 136 in the memory 138, or provided to an external device via the air interface 122, e.g., via the controller 136 from the memory 138, or directly from the environmental sensors 116 and 118, either as part of regular reporting or upon request from an external device.

The supply pack 100 includes one or more electronic displays that can be configured as electronic labels (or e-labels) 130 that can display information including text in human-readable form. For example, the e-labels 130 may be LCD displays or other forms of electronic paper. Electronic paper, for example, may offer certain advantages in being able to contain and display large amounts of information which is still visible when power is removed.

E-labels 130 may further be used to display machine-readable codes, such as bar codes, including two-dimensional bar codes. For example, safety information may include bar codes shown on an e-label 130, whereby a user may scan the bar code with a mobile computing device to obtain a web link for further information.

E-labels 130 may be used both to display dispensing information and safety information. Dispensing information may include, for instance, patient identifying information, medication name, a dosing regimen, and an expiry date of the dose units 112. A dosing regimen may include, for example, regularly scheduled dose times and quantities, suggested quantities and limits for as-needed use, and the like. Safety information may include, for example, instructions for administration, contra-indications, potential side effect to be aware of, and any other useful information or required disclosures.

E-labels 130 may be used to additionally to display clinical trial information such as an indication of a study protocol, a randomization code, and information identifying a clinical investigator. An indication of a study protocol may be a number, code, or name that refers to an entity conducting a study and/or documentation of the parameters of a study in which the patient is enrolled. Information identifying a clinical investigator may include a name or other identifier of a physician, a group of physicians, an institution, or a team responsible for oversight of the clinical study.

Supply Pack Labeling After Packaging

In contrast to printed labels and information, for example using in conventional clinical supply packs, the information to be contained on an individual supply pack 100 that contains an e-label 130 may be programmed after the supply pack 100 is sealed and crated for shipment. That is, the visible indications on an e-label 130 may be altered electronically after packaging at any point in the supply chain or in use. This is highly advantageous for improving logistics, in as much as clinical materials do not have to be mated to printed materials prior to distribution and dispensing. A single inventory of un-commissioned supply packs may be maintained, and then commissioned per particular requirements at the time of distribution, shipment, or dispensing.

For example, a single supply of supply packs may be maintained in a first country, and distributed equally to a variety of countries, including shipment through a variety of other countries. In particular, one or more supply packs, which can be included in a carton of supply packs, can be sent from a first country to a second country and, ultimately, a third country, for example, need not be labeled in the native language of the first or second country. Nor does the shipper of the first country need to know in advance whether the package is destined for the third country. Rather, each supply pack may be commissioned with required display information, in the language of the third country, either at the time of shipment from the first country, at the time of receipt in the third country, or at the time of dispensing. It is recognized that the supply packs can be sent from the first country to the second country which defines the destination country.

Custom Language and Multi-Language Display

Human readable information may be loaded into a supply pack in any language or in multiple languages, and displayed on an e-label 130. For example, in the case of clinical trials or recalls, safety information or administration instructions may be updated in the field long after manufacture of a supply pack 100. When a supply pack 100 dispensed for use by a patient, for example, information may be loaded in preferred language for the patient, an attending nurse or aid, and/or attending doctor, in addition to the language required by local law.

User Selection of Information for Display

A supply pack 100 may be arranged to alter which information is displayed on an e-label 130 in response to changing conditions or user requests. For example, the supply pack 100 may include inputs 132, such as momentary contact or capacitive sensing switches, or the like, which trigger action by the controller. An input 132 may have a dedicated function, such as browsing up or down when an e-label 130 presents a portion of a multi-page piece of information. Alternatively, the interpretation of input activation may depend on a text or image displayed and/or highlighted on the e-label 130. For example, an input 132 may be used to enlarge dosing or administration information, or to page down through multiple pages of safety information, or select a link within display information to go to particular information of interest, e.g., in the manner of a web page, rather than requiring a user to seek information in a large sheet of fine-print safety information.

Similarly, inputs 132 may be used to select different languages for the display of information. For example, a first input may be activated by a user to signal to the controller 136 to change which language in a list of languages is highlighted, and a second input may be activated by a user to indicate to the controller 136 that display in the currently highlighted language is preferred by the user.

Multiple e-labels 130, or multiple sections of a single e-label 130, may be used to separately display static information, e.g., in accordance with local regulatory requirements, and information selected by a user using inputs 132.

Display of Dynamic Information

Similarly, e-labels 130 can display information that is newly received or newly discovered by the supply pack 100. For example, the e-label 130 may be used to display a status of the clinical supply 110. In one example, a status of the clinical supply 110 can be a number of dose units 112 that have been removed or that remain in the clinical supply, for instance as sensed by the use sensors 114 and communicated to the controller 136 from the use sensors 114. Similarly, the e-label 130 can display dynamic information such as an expiry of the dose units 112 due to the passage of time, e.g., past the expiration date, or due sensing to one or more environmental conditions beyond safe limits as detected by one or more environmental sensors 116 and 118, e.g., due to heat, vibration, humidity, or exposure to light. In addition, an output 134, such as an LED indicator, may be used to indicate a state of the clinical supply 110, e.g., showing green if the clinical supply 110 is ready for use, or red if the clinical supply 110 is expired or otherwise determined to be unsuitable for current use.

Relabeling After Dispensing to a Patient

E-labels 130 can further display updated information even after one or more dose units 112 have been removed for consumption by the patient. For example, the supply pack 100 may communicate with a mobile communication device, such as a cell phone of a patient or care giver, via the air interface 122 and antenna 120 to receive updated dosing information (e.g., changes to the quantity of medicine to be administered, and the timing of the doses), administration instructions (e.g., changes to how dose units are to be used, such as before meal or after meals; changes to information to be recorded when using the clinical supply), or safety information (e.g., new contra-indications or side effects to be aware of). The received information can then be displayed on the e-label 130. Similarly, product recall information received by the supply pack 100 via the air interface 122 can be displayed on the e-label 130.

Multipack Operations

Figure 7:
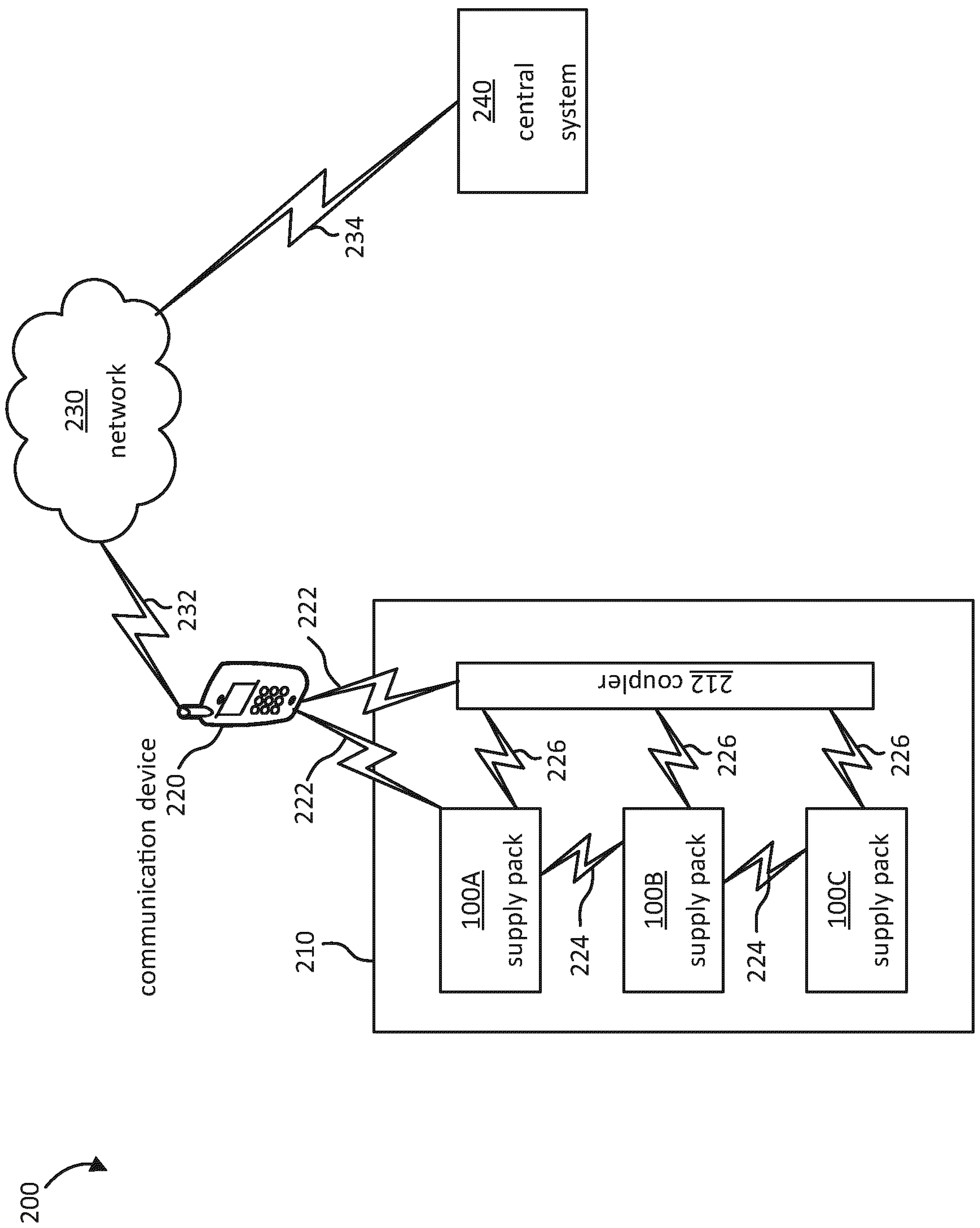
FIG. 7 is a block diagram of an example system including multiple supply packs in a multipack, a communication device, and a central system.

Referring now to FIG. 7, a communication system 200 can include at least one supply pack 100, a communication device 220 that is external with respect to the supply pack 100 and is configured to communicate with the at least one supply pack 100, and a central system 240 that is configured to communicate with the communication device 220 over a network 230. The at least one supply pack 100 can be provided individually, or in a multipack 210 that includes a plurality of supply packs 100, such as supply packs 100A, 100B, and 100C. The supply packs may be configured as described above with reference to FIG. 6.

The multipack 210 may be a shipper box, such as a cardboard carton, for example, or a plastic distribution tote box, that is used for the common transport of different clinical supply packs 100, where the shipper box has an additional shipping label that does not contain pharmaceutical labeling information, such as the information illustrated in FIGS. 2-5.

Alternatively, the multipack 210 may be an assembly comprising multiple supply packs 100, all bearing pharmaceutical labeling such as the information shown in FIGS.

2-5, e.g., where the clinical supply packs 100 are intended to be dispensed together for use by a single patient. In this case, the clinical supply packs 100 may be essentially identical, e.g., container doses of the same medication to be used over a course of treatment. Alternatively, the clinical supply packs 100 could each contain different clinical supplies, e.g., with set a bills in clinical supply pack 100A, a set of injectable medications in clinical supply pack 100B, and a set of specimen collection supplies in clinical supply pack 100C. Further, a multipack 210 may contain a nested set of clinical supply packs, e.g., where clinical supply pack 100A bears a master label, and clinical supply packs 100B and 100C are physically contained inside of clinical supply pack A, wherein clinical supply packs each have their own label in addition to the label of clinical supply pack A. A multipack 210 may include a hierarchy of supply packs at multiple tiers, e.g., to facilitate organized distribution of supplies over a course of treatment, with individual labeling, tracking, etc., for each pack in the hierarchy.

The external device, which can be the communication device 220, is able to communicate with one or more of the supply packs 100. For instance, the communication device can communicate wirelessly with the one or more supply packs 100. The communication device 220 is also in communication with the central system 240 over the network 230. The network 230 can be any suitable wireless or other data communication network.

A communication device 220 be specially adapted for use with the supply packs 100A, 100B, and 100C, and/or with the central system 240, through specialized hardware, data, or software. For example, the communication device 220 may have an RFID (radio-frequency identification) reader for communicating with the controller 136 of a supply pack. A communication device may be provisioned with certificates or other information necessary for establishing secure communications with the supply packs 100A, 100B, and 100C and/or the central system 240. The communication device 220 may use a software application or web service which enables it to communicate with the supply packs 100A, 100B, and 100C and/or the central system 240. The certificates and software, for example, may be tailored for use in a particular health care system, clinical setting, or clinical study, for example.

In the example of FIG. 7, the communication device 220 can belong to the user, such as the patient or caretaker of the patient. The communication device can be configured as a cellular telephone, such as an application of the cellular telephone, but it should be appreciated that communication device 220 may alternatively be any suitable mobile computing device, such as a tablet, laptop, or scanner, for example, or a fixed computer such as a desktop or industrial fixture. Preferably, the communication device 220 communicates with the multipack 210 and/or the supply packs 100 via non-line-of-sight wireless links 222, but may alternatively use, e.g., infrared or wired connections, for instance. Thus, the communication device 220 can communicate with the multipack 210 via non-line-of-sight or line-of sight wireless data communication links 222. Alternatively, the communication device 220 can communicate with the multipack 210 via one or more data communication wires.

In the example of FIG. 7, the communication device 220 communicates via a wireless link 232 with the network 230, and the network 230 communicates with the central system 240 via a wireless link 234. For example, link 232 may be a WiFi, BlueTooth, or cellular communications link, and link 234 may also be a similar or different link. In practice, any wireless, wired, optical, or other computer linkage may be employed, and the network 230 and central system 240 may be arranged in a variety of ways. For example, the network 230 may encompass both a local WiFi gateway and the Internet, and the central system 240 may encompass a network of apparatuses including a manufacturers enterprise system and computers used by clinical investigators, pharmacists, and attending physicians.

In the example of FIG. 7, the multipack 210 can include a coupler 212, which may include, for example, an active or passive antenna device, that is helpful in coupling or repeating signals between the supply packs 100 and the communication device 220, and/or from supply pack to supply pack. The communication device 220 may communicate directly with one or more supply packs 100, or communicate with one or more couplers 212 that can, in turn, communicate with, or otherwise relay signal to, one or more supply packs 100.

The system 200 may be used in a variety of scenarios. The system 200 may be used at the time of manufacture, e.g., when the components of the supply pack 100 are brought together. The system 200 may be used at distribution, e.g., when supply packs are stored and shipped singly or in multipacks 210. The system 200 may be used at the time of dispensing, e.g., when one or more supply packs 100 are given from a dispensary for use by a specific patient, e.g., in a clinical setting or a pharmacy. The system 200 may be used during use of a supply pack 100 by a patient, e.g., to allow updated information to be provided to the patient and others via display on the e-label 130, and information to be collected from the supply pack 100 to the communication device 220 and central system 240. The system 200 may be used in post-use analysis, e.g., after a used supply pack 100 is collected from a treatment area, e.g., for the extraction of environmental sensor data or test materials or samples stored in the supply pack 100. The system 200 may be used to relabel an unused supply pack 100.

Notably, different information for different supply packs may be provided to the supply packs after they have been combined in the multipack 210. This may occur at any point in the life cycle of the clinical supply packs 100. For example, supply packs 100A and 100B may be provided with information for a first patient, while supply back 100C is provided with information for a second patient. Similarly, supply packs 100A and 100B may be labeled for a first and second treatment of the same patient, for instance.

In addition to having different patient identifying information and different dosing information, one or more of the supply packs 100A, 100B, and 100C may be identified for use in a different country than at least one other of the supply packs 100A, 100B, and 100C. Accordingly, in accordance with local regulatory requirements, the one or more of the supply packs 100A, 100B, and 100C may have different information than the at least one other of the supply packs 100A, 100B, and 100C. The different information can include at least one or more up to all of a different expiration date, different handling requirements, different administration instructions, and/or, if applicable, a different clinical trial investigator, protocol, and randomization kit number. Further, the different information can be displayed in different languages or different sets of languages on each of the supply packs 100A, 100B, and 100C.

The information for each of the supply packs 100 may pass directly from the communication device 220 to an intended supply pack 100 of the plurality of supply packs 100, e.g., via the wireless link 222. Similarly, the information for each pack may pass to the intended supply pack 100 via one or more intermediary packs or couplers, or a combination thereof. For example, information for an intended supply pack 100B may be received by supply pack 100B from an intermediate supply pack 100A via a link 224 between the supply packs 100A and 100B. Alternatively, information for the intended supply pack 100B can be received from the intermediate supply pack 100A, or indirectly, e.g., first via a link 222 from the communication device 220 to the coupler 212, from the coupler 212 via a link 226 to supply pack. 100A or 100C, then supply pack 100B from supply pack 100A or 100C, for example.

Information gathered by individual supply packs 100 may be collected by the communication device 220 and then processed by the communication device 220, and/or forwarded to the central system 240 for processing. For example, information gathered may include use sensor data, environmental sensor data, and entries made by users via input switches along with the context of displayed information when the entries are made by users.

An update may be passed from the communication device 220 to a supply pack 100 based on information from the communication device 220, central system 240, or in response to information received from the supply pack 100. For example, an update may include revised dosing, dose administration, and/or safety information. Additionally, or alternatively, an update may include a new expiration date or new limits for determining when environment sensor readings exceed safety requirements.

The central system 240 may pre-position information intended for a particular supply pack 100 or set of supply packs 100, whereby the information is first transferred to the communication device 220, and later transferred from the communication device 200 next communicates with the particular supply pack 100 or set of supply packs 100. Similarly, a supply pack 100 may store information in anticipation of establishing a connection with a communication device 220. The communication device 220 can communicate with the at least one supply pack 100 when the communication device 220 is brought within a predetermined proximity with respect to the at least one supply pack 100. Alternatively, or additionally, the user can select an input on one or both of the communication device 220 and the at least one supply pack 100 that establishes a connection between the communication device 220 and the supply pack 100.

In one example, the supply pack 100 can be a passive supply pack that does not include an independent power source, such as a battery. Rather, the passive supply pack 100 can be powered by harvesting energy from a near-field communications link with a communication device 220. Thus, the passive supply pack 100 may have no capacity to run a clock to independently determine the passage of time. However, the supply pack 100 may have a record of an expiration date of the pharmaceutical dose units 112, and may receive time and date information from the communication device 220 upon connection with the communication device 220. The supply pack 100 may then determine that its clinical supply 100 has expired, and alter an e-label 130 display accordingly. Similarly, the supply pack 100 may use energy at the time of connection and/or processing power of the communication device 220 to evaluate data from use sensors 114 and/or one or more environmental sensors 116 and 118 to make determinations as to conditions of the clinical supply 110.

Similarly, a supply pack may register a request for information, or a request to record a condition, received from a user via an input 132 of the supply pack 100, and then transfer information to the communication device 220 when the supply pack 100 is connected to the communication device 220. The request can be processed by the communication device 220 or communicated from the communication device 220 to the central system 240. For example, a user may request information in a language not originally provisioned in the supply pack 100 at the time of dispensing, and the supply pack may later request such information upon later connecting to communication device 220. The communication device 220 may then provide the information, either immediately or after requesting and receiving the information from the central system 240.

In other examples, the supply pack 100 can be an active supply pack that has a power source and can independently determine the passage of time and thus can determine when the expiration date of the pharmaceutical dose units 112 has been reached without being in communication with the communication device 220, and can communicate the determination to the communication device 220.

Re-Labeling of Unused Clinical Materials after Dispensing

A supply pack 100 with an e-label 130 may dispensed to a second patient, even after the dispensing of the supply pack 100 for use by a first patient. In contrast, generally dispensed clinical materials with printed labels must be destroyed if not used by the patient to whom they are dispensed. Electronic labeling allows, for example, in accordance with communications security protocols, a communication device 220 to communicate with the supply pack 100 and retrieve information regarding the use and safety of the clinical supply 110, e.g., as determined by use sensors 114 and environmental sensors 116 and 118. Further, via an input 132 the processor may have information provided by a user that the supply pack 100 is in some way defective. If the external device is satisfied that the supply pack 100 is in good condition, and/or the processor 136 is satisfied that the supply pack 100 is in good condition, new patient, safety, and/or clinical trial information may be downloaded to, and displayed by, the supply pack 100 on an e-label 130.

Communications Flow

Figure 8:
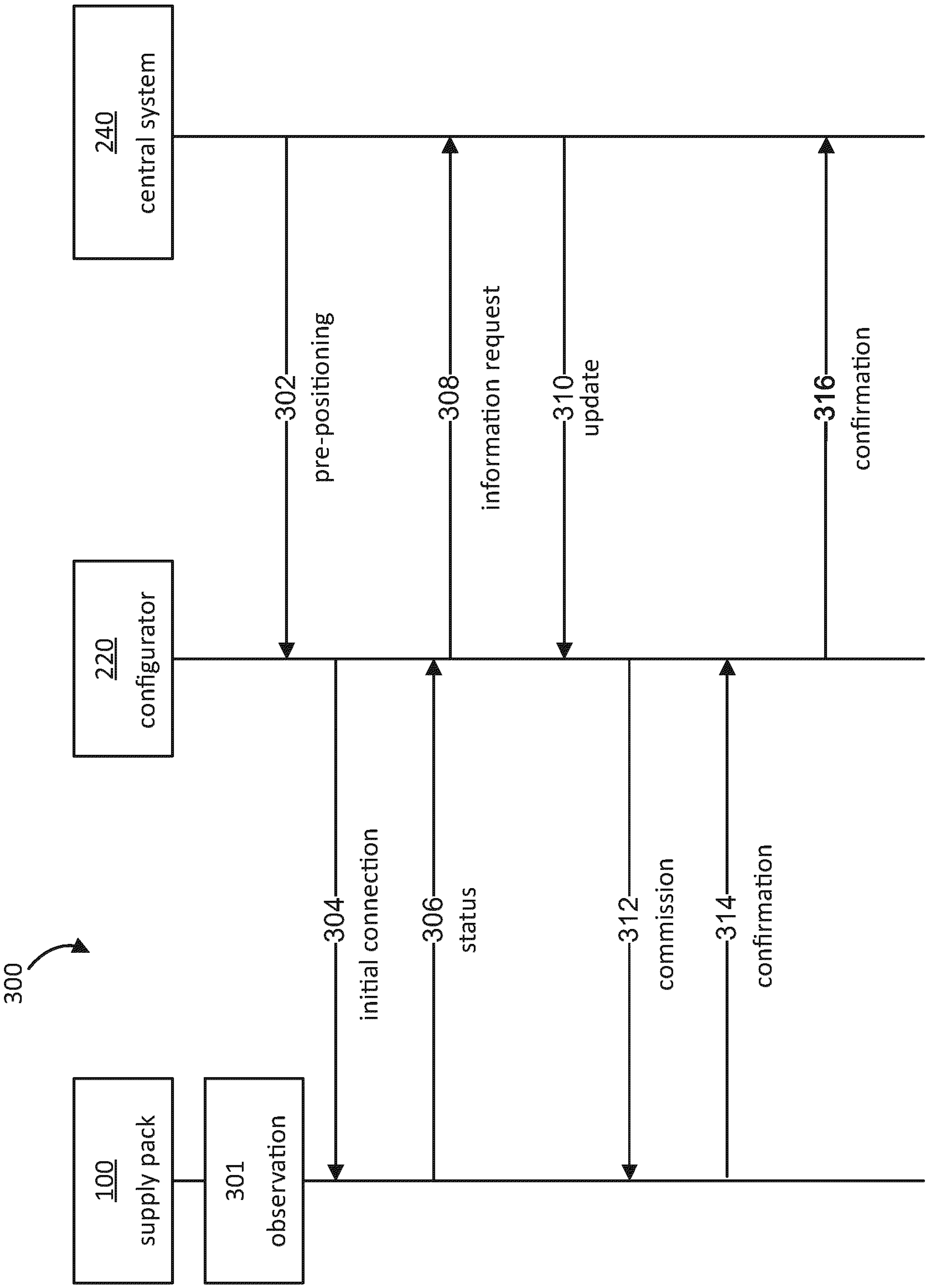
FIG. 8 is a call flow of an example set of interactions among a clinical supply pack, a supply pack communication device, and a central system.

Referring now to FIG. 8, an example communications flow 300 which may apply in a number of situations. For purposed of illustration, the supply pack 100 of FIG. 8 is similar to those discussed in relation to FIGS. 1 and 2, and the communication device 220 and central system 240 are as described in connection with FIG. 7.

The communications flow 300 can include step 301, in which the supply pack 100 may make observations of its conditions, e.g., via observation of use sensors 114, environmental sensors 116 and 118, and inputs 132. The observation may include time at which an input 132 was activated and/or what was displayed on an e-label 130 at the time that an input 132 was actuated. For example, the meaning of an input 132 may vary based on whether the input 132 was actuated in response to: a prompt to select a language for display, a link to further information; or a selection to multiple-choice prompt regarding the patient, a symptom, or an aspect of administering a dose. Similarly, a supply pack 100 may make an observation regarding an environmental sensor reading, an environmental sensor reading outside of a safe storage requirement, a period of time over which a reading was observer, or a combination thereof.

At step 302, the central system 240 may pre-position information with the communication device 220. For example, the central system 240 may send information to a communication device in anticipation of one or more supply packs 100 being shipped by a distributor and/or received at a dispensary. This obviates the need for a live connection between the communication device 220 and the central network 240 at the time of labeling and/or configuring the supply pack 100.

At step 304, the communication device 220 is placed in communication with the supply pack 100. In one example, the communication device 220 can initiate communication with the supply pack 100. For example, the communication device 220 may send a broadcast to discover supply packs within range, and then negotiate a connection with any supply pack it finds, and form a secure link to any supply pack it wishes to configure. The communication device 220 may send initial information relating to its identity, credentials, time and date, etc. Alternatively, the supply pack 100 can initiate communication with the communication device 220.

Once the communication device 220 and the supply pack 100 are in communication with each other, the supply pack may send a status report to the communication device 220 at step 306. The status report may include such items as the identity and credentials of the supply pack, its current commission information, if any, such as patient, safety, and clinical trial information, expiry, information from any of the sensors, user inputs, and/or requests for information of the type described above.

In step 308, in response to information in the initial connection or status report, the communication device 220 may request information from the central system 240. For example, if a user of the supply pack has indicated, e.g., via actuation of an input 132, a request for display in a language not currently available in the supply pack 100, or for other information associated with a selected link displayed on an e-label 130, and such information is not available in the communication device 220, the communication device 220 may request the information from the central system.

Alternatively, or additionally in step 308, the communication device 220 may report information received from the supply pack 100, such as the expiry, use, or condition of the clinical supply 110 of the supply pack 100, to the central system 240.

In step 310, the central system 240 may send an information update to the communication device 220, e.g., to respond to one or more requests by the supply pack 100 with information requested, or otherwise send information that is desired to be communicated to the supply pack, or otherwise still send data to the supply pack 100 in response to the status of the supply pack 100. The information can be sent from the central system 240 to the communication device 220, which in turn sends the information to the supply pack 100 when the communication device 220 is in communication with the supply pack 100. For example, the central system 240 may inform the communication device 220 that the supply pack 100 labeled for a first patient is to be diverted to a second patient, marked for destruction or return for analysis, or provided with update safety, dosage, language, administration, clinical study, or other information, such as an updated expiration date of the pharmaceutical dose units 112.

Similarly, the central system 240 may inform the communication device 220 of a product state of the supply pack 100. The product state may indicate, for example, whether the supply pack 100 is fit or unfit for use. Additionally or alternatively, the product state may include information regarding a product recall, expiration, or other condition affecting the fitness of the supply pack 100. The supply pack 100 may display the product state on an electronic label. Alternatively, the supply pack 100 may use the product state to determine how to adjust its labeling, e.g., to display an expiration notice in a preferred language based on the product state, a record of a preferred language, and a selection of available label messages.

In step 312, the communication device 220 provides the supply pack 100 with patient, safety, and/or clinical trial labeling information, and information for monitoring of inputs and/or sensors, managing displays, and activating outputs. Such information may come from the central system 240, or from other sources, such as a user interface of the communication device 220.

For example, the supply pack may have a unique identifier, e.g., associated with the controller 136 of the supply pack, which may be used in the establishment of secure communications between the supply pack 100 and the communication device 220, and for identifying the supply pack 100 to the central system 240. Alternatively, or additionally, the supply pack 100 may be commissioned by the communication device with serialization information for display on an e-label 130 and for quality control tracking purposes.

In step 314, the supply pack 100 may send a confirmation that all of the commission information has been duly received.

In step 316, the communication device 220 may send a confirmation to the central system that the supply pack 100 has been commissioned in accordance with pre-positioned or updated information provided by the central system 240.

Variations

The flow 300 of FIG. 8 may be followed at different times with different equipment playing different roles of communication device 220 and central system 240. For example, at manufacture the communication device 220 may be an industrial fixture in a pharmaceutical production facility, and the central system may be a portion of an enterprise computing system. At distribution, e.g., at a warehousing facility handling storage and shipment of supply packs, the communication device 220 may be a desktop computer. When the supply pack 100 has been delivered to a pharmacy for subsequent delivery to the user, the communication device 220 may be a bar code scan gun, enhanced with near-field wireless capability, for example, operating in conjunction with a pharmacy checkout system. When the supply pack 110 has been delivered to the user for the removal and consumption of the pharmaceutical dose units 112, the communication device 220 may be a cell phone or other mobile device belonging to the user, such as a patient, or a care giver such as an attending physician. The central system 240 may be based in a centralized facility monitoring an international set of clinical trials, for instance, or a laptop computer of an investigator at a single facility. It will be appreciated that many arrangements of computing equipment may be used to implement the techniques described herein.

Example Computing Devices

Figure 9:
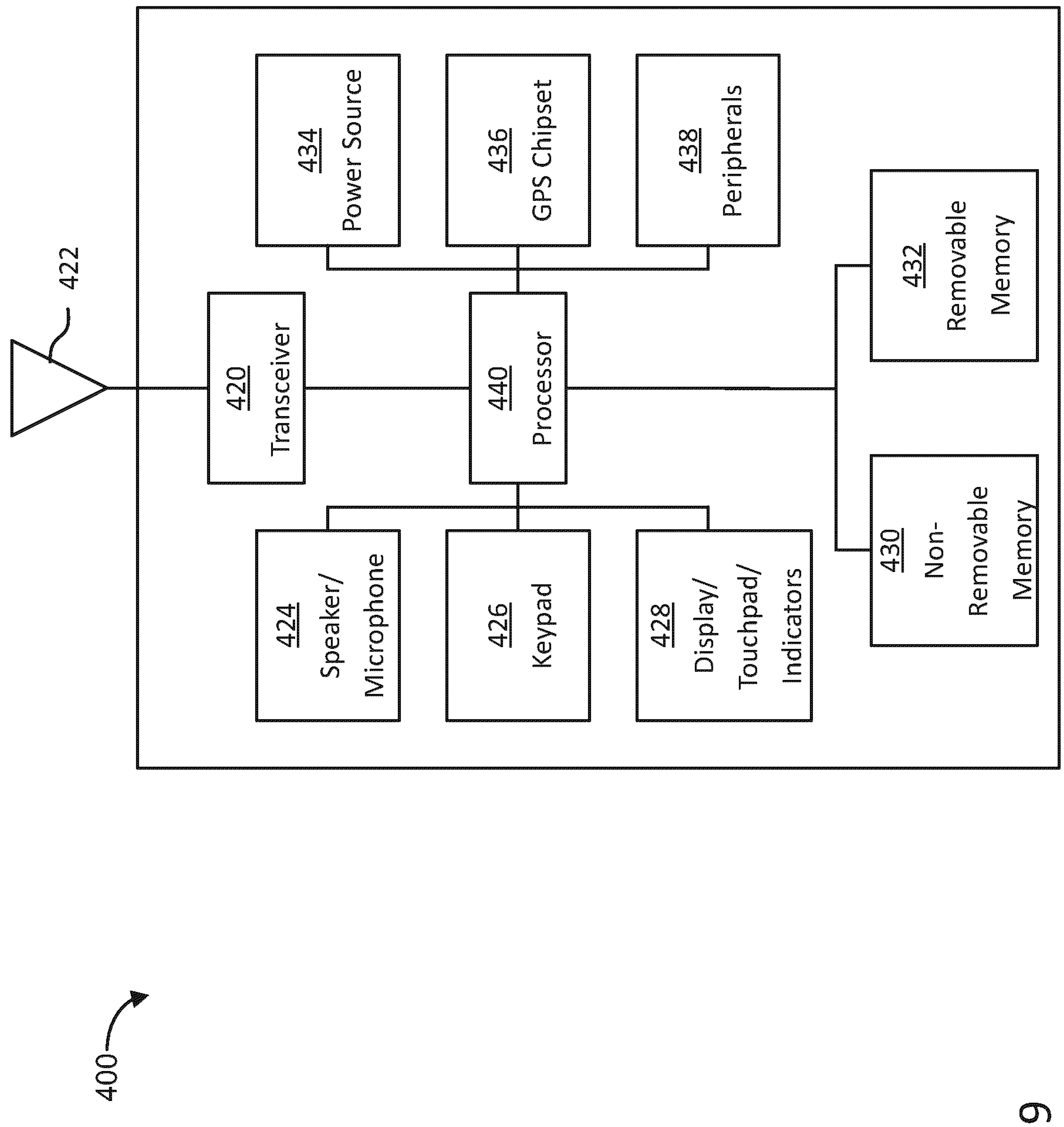
FIG. 9 is a block diagram of an example communication device.
Figure 10:
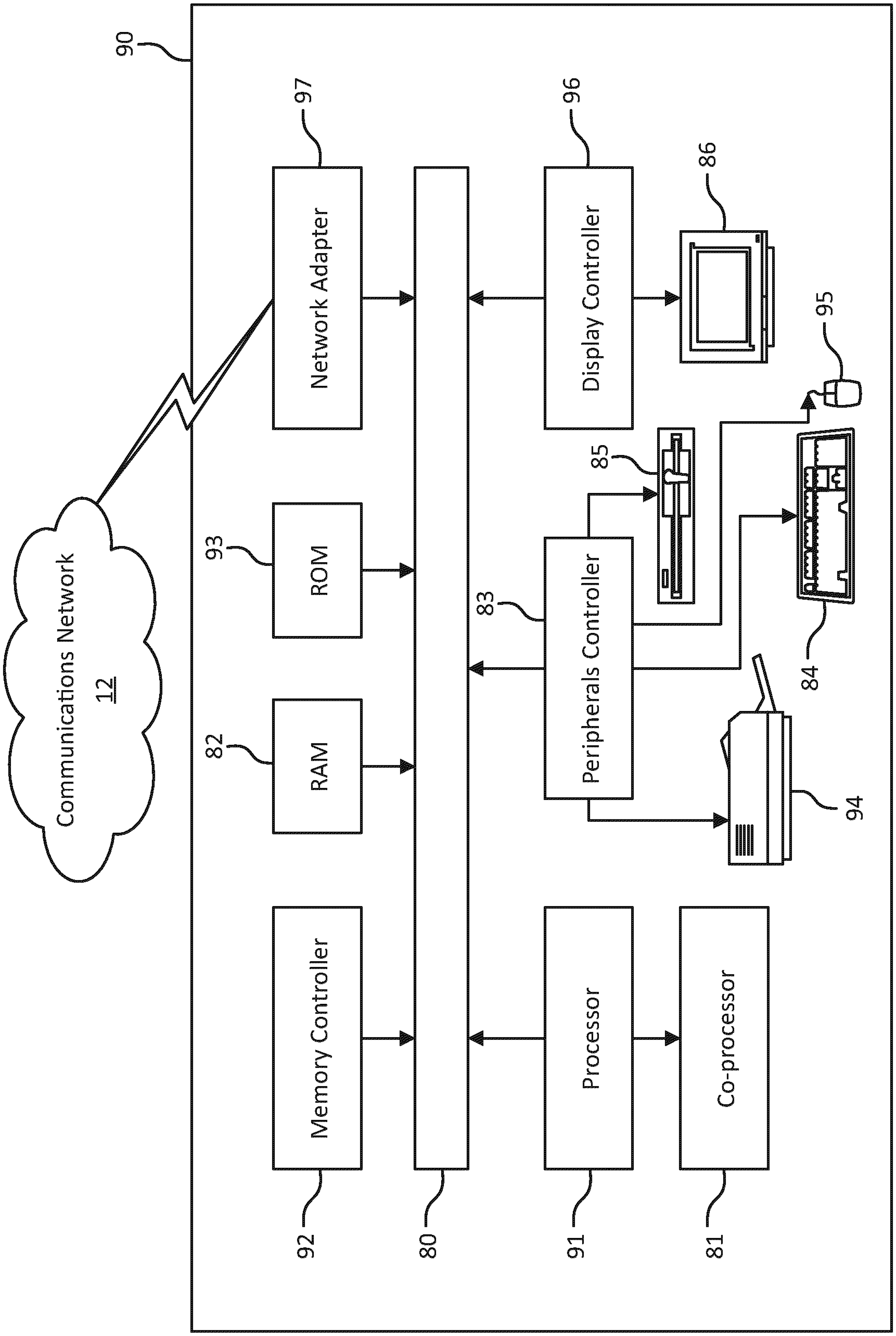
FIG. 10 is a block diagram of an example computing device.

FIG. 9 is a block diagram of an example apparatus 400 that may be configured for wireless communications and operations in accordance with the systems, methods, and apparatuses described herein, such as the communication device 220 of FIG. 7 and FIG. 8. As shown in FIG. 9, the example apparatus 400 may include a processor 440, a transceiver 420, a transmit/receive element 422, a speaker/microphone 424, a keypad 426, a display/touchpad/indicators 428, non-removable memory 430, removable memory 432, a power source 434, a global positioning system (GPS)

chipset 436, and other peripherals 438. It will be appreciated that the apparatus 400 may include any sub-combination of the foregoing elements.

The processor 440 may be a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Array (FPGAs) circuits, any other type of integrated circuit (IC), a state machine, and the like. The processor 440 may perform signal coding, data processing, power control, input/output processing, and/or any other functionality that enables the apparatus 400 to operate in a wireless environment. The processor 440 may be coupled to the transceiver 420, which may be coupled to the transmit/receive element 422. While FIG. 9 depicts the processor 440 and the transceiver 420 as separate components, it will be appreciated that the processor 440 and the transceiver 420 may be integrated together in an electronic package or chip.

In practice, the apparatus 400 may have multiple transceivers and/or antennas or communications in multiple frequency bands, such as near-field and other RFID frequencies, BlueTooth, WiFi, and cellular communications bands, or example.

The processor 440 of the apparatus 400 may be coupled to, and may receive user input data from, the speaker/microphone 424, the keypad 426, and/or the display/touchpad/indicators 428 (e.g., a liquid crystal display (LCD) display unit or organic light-emitting diode (OLED) display unit. The processor 440 may also output user data to the speaker/microphone 424, the keypad 426, and/or the display/touchpad/indicators 428. In addition, the processor 440 may access information from, and store data in, any type of suitable memory, such as the non-removable memory 430 and/or the removable memory 432. The non-removable memory 430 may include random-access memory (RAM), read-only memory (ROM), a hard disk, or any other type of memory storage device. The removable memory 432 may include a subscriber identity module (SIM) card, a memory stick, a secure digital (SD) memory card, and the like. The processor 440 may access information from, and store data in, memory that is not physically located on the apparatus 400, such as on a server that is hosted in the cloud or in an edge computing platform or in a home computer (not shown).

The processor 440 may receive power from the power source 434, and may be configured to distribute and/or control the power to the other components in the apparatus 400. The power source 434 may be any suitable device for powering the apparatus 400. For example, the power source 434 may include one or more dry cell batteries, solar cells, fuel cells, and the like.

The processor 440 may also be coupled to the GPS chipset 436, which may be configured to provide location information (e.g., longitude and latitude) regarding the current location of the apparatus 400. In addition to, or in lieu of, the information from the GPS chipset 436, the apparatus 400 may receive location information over the air interface from a base station, e.g., a WiFi base station, and/or determine its location based on the timing of the signals being received from two or more nearby base stations.

The processor 440 may further be coupled to other peripherals 438, which may include one or more software and/or hardware modules that provide additional features, functionality, and/or wired or wireless connectivity. For example, the peripherals 438 may include various sensors such as an accelerometer, biometrics (e.g., finger print) sensors, an e-compass, a satellite transceiver, a digital camera (for photographs or video), a universal serial bus (USB) port or other interconnect interfaces, a vibration device, a television transceiver, a hands free headset, a Bluetooth module, a frequency modulated (FM) radio unit, a digital music player, a media player, a video game player module, an Internet browser, and the like.

The apparatus 400 may be included in other apparatuses or devices, such as a sensor, consumer electronics, a wearable device such as a smart watch or smart clothing, a medical or eHealth device, a robot, industrial equipment, a drone, a vehicle such as a car, truck, train, or an airplane. The apparatus 400 may connect to other components, modules, or systems of such apparatuses or devices via one or more interconnect interfaces, such as an interconnect interface that may comprise one of the peripherals 438.

FIG. 5 is a block diagram of an exemplary computing system 90 which may be used as, or as part of, the central system 240 of FIG. 7 and FIG. 8. Computing system 90 may comprise a computer or server and may be controlled primarily by computer readable instructions, which may be in the form of software, wherever, or by whatever means such software is stored or accessed. Such computer readable instructions may be executed within a processor 91, to cause computing system 90 to do work. The processor 91 may be a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Array (FPGAs) circuits, any other type of integrated circuit (IC), a state machine, and the like. The processor 91 may perform signal coding, data processing, power control, input/output processing, and/or any other functionality that enables the computing system 90 to operate in a communications network. Coprocessor 81 is an optional processor, distinct from main processor 91, that may perform additional functions or assist processor 91. Processor 91 and/or coprocessor 81 may receive, generate, and process data related to the methods and apparatuses disclosed herein.

In operation, processor 91 fetches, decodes, and executes instructions, and transfers information to and from other resources via the computing system's main data-transfer path, system bus 80. Such a system bus connects the components in computing system 90 and defines the medium for data exchange. System bus 80 typically includes data lines for sending data, address lines for sending addresses, and control lines for sending interrupts and for operating the system bus. An example of such a system bus 80 is the PCI (Peripheral Component Interconnect) bus.

Memories coupled to system bus 80 include random access memory (RAM) 82 and read only memory (ROM) 93. Such memories include circuitry that allows information to be stored and retrieved. ROMs 93 generally contain stored data that cannot easily be modified. Data stored in RAM 82 may be read or changed by processor 91 or other hardware devices. Access to RAM 82 and/or ROM 93 may be controlled by memory controller 92. Memory controller 92 may provide an address translation function that translates virtual addresses into physical addresses as instructions are executed. Memory controller 92 may also provide a memory protection function that isolates processes within the system and isolates system processes from user processes. Thus, a program running in a first mode may access only memory mapped by its own process virtual address space; it cannot access memory within another process's virtual address space unless memory sharing between the processes has been set up.

In addition, computing system 90 may contain peripherals controller 83 responsible for communicating instructions from processor 91 to peripherals, such as printer 94, keyboard 84, mouse 95, and disk drive 85.

Display 86, which is controlled by display controller 96, is used to display visual output generated by computing system 90. Such visual output may include text, graphics, animated graphics, and video. The visual output may be provided in the form of a graphical user interface (GUI). Display 86 may be implemented with a CRT-based video display, an LCD-based flat-panel display, gas plasma-based flat-panel display, or a touch-panel. Display controller 96 includes electronic components required to generate a video signal that is sent to display 86.

Further, computing system 90 may contain communication circuitry, such as for example a wireless or wired network adapter 97, that may be used to connect computing system 90 to an external communications network or devices, e.g., to communicate with other network devices and, via network connections, to WiFi, cellular, and other networks to connect with a communication device such as communication device 240 of FIG. 7 and FIG. 8.

We claim:

1. A first clinical supply pack, comprising:

packaging;

at least one specimen collection supply;

a supply of clinical product stored in at least one storage container, the at least one storage container and at least one specimen collection supply being sealed within the packaging for distribution;

an electronic label disposed on the packaging and having an electronic display that selectively displays images and/or text for viewing and comprehension by a user;

a processor in communication with the electronic label;

wireless communication circuitry in communication with the processor;

a memory in communication with the processor; and computer-executable instructions stored in the memory which, when executed by the processor, cause the first clinical supply pack to:

establish a wireless communications link with a communication device;

receive, from the communication device via the wireless communications link while the first clinical supply pack is sealed for distribution, labeling information comprising information regarding a first patient, a dosing regimen, and safety information, the dosing regimen and the safety information being provided in a first language according to regulatory requirements for a region in which the first patient receives treatment;

visually display the labeling information on the electronic display of the electronic label;

receive, from the communication device via the wireless communications link while the first clinical supply pack is sealed for distribution, a set of labeling rules comprising an expiration date of the supply of clinical product, and further receive a serialization of the first clinical supply pack;

adjust the labeling information displayed on the electronic display in accordance with the labeling rules;

receive, from the communication device via the wireless communications link, labeling status information comprising a product state; and adjust the labeling information displayed on the electronic display in accordance with the product state.

2. The first clinical supply pack of claim 1, wherein the instructions further cause the first clinical supply pack to establish the communications link with communication device via a wireless communications link with a second clinical supply pack.

3. The first clinical supply pack of claim 1, wherein the instructions further cause the first clinical supply pack to receive, from the communication device via the wireless communications link, the dosing regimen and the safety information in a second language.

4. The first clinical supply pack of claim 1, wherein the instructions further cause the first clinical supply pack to display a notice of expiration based on evaluation of a labeling rule.

5. The first clinical supply pack of claim 1, wherein the instructions further cause the first clinical supply pack to receive, from the communication device via the wireless communications link, and to display, updated labeling status information received by the communication device from a central system, the labeling status information pertaining to a product recall or expiration.

6. The first clinical supply pack of claim 1, wherein the instructions further cause the first clinical supply pack to display an updated dosing regimen received from a central system via the communication device over the wireless communications link.

7. The first clinical supply pack of claim 1, wherein the instructions further cause the first clinical supply pack to provide, to a central system via the wireless communications link to the communication device, clinical supply usage or environmental information.

8. The first clinical supply pack of claim 1, wherein the instructions further cause the first clinical supply pack to receive, from the communication device via the wireless communications link, and to display, clinical trial information comprising an identifier of an investigator, an identifier of a subject, and an identifier of a study protocol.

9. The first clinical supply pack of claim 1, wherein the instructions further cause the first clinical supply pack to report, to a central management system for a clinical trial via the communication device, clinical supply usage or environmental information.

10. The first clinical supply pack of claim 1, wherein the instructions further cause the first clinical supply pack to receive, from the communication device via the wireless communications link, the dosing regimen and the safety information in a second language in response to an input device of the clinical supply pack.

11. The first clinical supply pack of claim 1, wherein the at least one specimen collection supply comprises at least one swab, at least one test strip, at least one sample container, at least one needle, or any combination thereof.

12. A method, comprising:

establishing, at a clinical supply pack, a wireless communications link with a communication device, the clinical supply pack comprising (i) packaging, (ii) at least one specimen collection supply, (iii) a supply of clinical product stored in at least one storage container, that at least one container and at least one specimen collection supply being sealed within the packaging for distribution, (iv) a processor, and (v) an electronic label disposed on the packaging and having an electronic display;

receiving, from the communication device via the wireless communications link while the first clinical supply pack is sealed for distribution, labeling information comprising information regarding a first patient, a dosing regimen, and safety information, the dosing regimen and the safety information being provided in a first language according to regulatory requirements for a region in which the first patient receives treatment;

visually displaying the labeling information on the electronic display of the electronic label in a form of images and/or text for viewing and comprehension by a user;

receiving, from the communication device via the wireless communications link while the first clinical supply pack is sealed for distribution, a set of labeling rules comprising an expiration date of the supply of clinical product, and further receive a serialization of the first clinical supply pack;

adjusting the labeling information visually displayed on the electronic display in accordance with the labeling rules;

receiving, from the communication device via the wireless communications link, labeling status information comprising a product state; and adjust the labeling information visually displayed on the electronic display in accordance with the product state.

13. The method of claim 12, wherein the instructions further cause the first clinical supply pack to receive, from the communication device via the wireless communications link, the dosing regimen and the safety information in a second language in response to an input device of the clinical supply pack.

14. The method of claim 12, wherein the instructions further cause the first clinical supply pack to receive, from the communication device via the wireless communications link, and to display, updated labeling status information received by the communication device from a central system, the labeling status information pertaining to a product recall or expiration.

15. The method of claim 12, wherein the instructions further cause the first clinical supply pack to receive, from the first clinical supply pack via the wireless communications link, and to display, an updated dosing regimen received by the communication device from a central system.

16. The method of claim 12, wherein the instructions further cause the first clinical supply pack to provide, to a central system via the wireless communications link to the communication device, clinical supply usage or environmental information.

17. The method of claim 12, wherein the instructions further cause the first clinical supply pack to receive, from the communication device via the wireless communications link, and to display, clinical trial information comprising an identifier of an investigator, an identifier of a subject, and an identifier of a study protocol.

18. The method of claim 12, wherein the instructions further cause the first clinical supply pack to report, to a central management system for a clinical trial via the communication device, the clinical supply usage or environmental information.

19. The method of claim 12, wherein the at least one specimen collection supply comprises at least one swab, at least one test strip, at least one sample container, at least one needle, or any combination thereof.

* * * * *